United States Patent

Hamada

(10) Patent No.: US 8,075,579 B2
(45) Date of Patent: Dec. 13, 2011

(54) PEDICLE DART SYSTEM

(75) Inventor: James S. Hamada, Torrance, CA (US)

(73) Assignee: Life Spine, Inc., Hoffman Estates, IL (US)

(*) Notice: Subject to any disclaimer, the term of this patent is extended or adjusted under 35 U.S.C. 154(b) by 1001 days.

(21) Appl. No.: 12/009,496

(22) Filed: Jan. 17, 2008

(65) Prior Publication Data

US 2009/0187220 A1   Jul. 23, 2009

(51) Int. Cl.
*A61B 17/32* (2006.01)
(52) U.S. Cl. .......................... 606/167; 606/300
(58) Field of Classification Search ............... 606/61, 606/71–72, 86 A, 99, 167, 300
See application file for complete search history.

(56) References Cited

U.S. PATENT DOCUMENTS

| | | | |
|---|---|---|---|
| 5,171,279 | A | 12/1992 | Mathews |
| 6,175,758 | B1 | 1/2001 | Kambin |
| 7,494,489 | B2* | 2/2009 | Roh ............ 606/86 A |
| 2005/0251139 | A1* | 11/2005 | Roh ................ 606/61 |
| 2006/0079903 | A1 | 4/2006 | Wong |
| 2007/0016219 | A1 | 1/2007 | Levine |
| 2008/0086140 | A1* | 4/2008 | Wolf .............. 606/79 |
| 2009/0254131 | A1* | 10/2009 | Roh ............ 606/86 A |

FOREIGN PATENT DOCUMENTS
WO   WO 2009/091616 A3   7/2009

OTHER PUBLICATIONS

Written Opinion of the International Searching Authority for PCT/US2009/000393, dated Aug. 27, 2009, 6 pages.

* cited by examiner

*Primary Examiner* — Suzette J Gherbi
(74) *Attorney, Agent, or Firm* — Foley & Lardner LLP (57) ABSTRACT

Minimal Invasive Spine Surgery (MISS) as a surgical approach is increasingly utilized because of the advantages it offers over conventional spine surgery. The smaller incision results in decreased tissue damage, less blood loss, decreased hospital stay & faster postoperative recovery. The drawbacks of MISS are the long learning curve of working through a smaller incision, longer length of surgery, & potential higher complication rate due to compromised visual field. These limitations can be overcome by more effectively using imaging and navigational devices. The pedicle device simplifies the hardest part of MISS instrumented fusion of conventional pedicle screw insertion by introducing a percutaneous temporary device to locate and create the channel for later conventional pedicle screw implantation using available imaging techniques. This results in faster conventional pedicle screw insertion with precision, thereby decreasing implantation error and minimizing soft tissue injury and blood loss, as well as neurological, vascular, and dural injuries and complications.

11 Claims, 9 Drawing Sheets

PEDICLE DART SYSTEM

FIELD OF THE INVENTION

The present invention relates to improvements in the field of spine and more particularly to a system for location, placement, and insertion of pedicle darts which is applicable to both MIS and open surgical technique which allows for more exacting and rapid placement and angular insertion of fixation members into the spinal pedicle, to facilitate one of the most difficult phases of spine surgery. Greater access, angularity and location is allowed independent of manipulation of the pedicle darts into bony tissue, resulting in a reduced time necessary to complete one of the more difficult phases of the operative procedure. The result is increased safety of placement and insertion, as well as less time spent on the operating table.

BACKGROUND OF THE INVENTION

Lumbar Diskectomy and other spinal techniques require external stabilization of lumbar vertebrae to either side of the vertebra being treated. Traditional pedicle screw insertion has required the identification of the correct insertion point for pedicle screw placement. This process is difficult, even where there is direction visualization of the area of the pedicle where insertion will occur. Because placement, angularity, and turning insertion is a complex process, the insertion process often leads to inaccurate placement of the screw. Such inaccurate placement can have serious neurological, vascular, and dural leak complications.

Further, inaccurate placement of the pedicle screw may result in damage such that screw insertion either cannot be achieved, or if it can be achieved it may require additional surgical procedures for correction and may not enable the holding strength necessary.

Conventional techniques for insertion of the pedicle screw may involve extensive paraspinous muscle dissection, impairment of surrounding tissue and other compromising tissue removal is commonly necessary to properly insert a pedicle screw. This most often results in significant blood loss during this exposure phase of the operation, which is only one part of a multiple step operative procedure. Any problems at any stage of an operation can risk the patient's health and compound any unexpected routine problems which occur.

The surgical practitioner is faced with the choice between high exposure and a good view, versus a more limited exposure with a much poorer view and a heightened risk of a wrong insertion of the pedicle screw. Further, when a high exposure is attempted, excess bleeding is often encountered directly due to the higher exposure which can even further obscure visualization and may require blood transfusion with its associated complications.

Any extra time on the operating table, whether caused by excess bleeding or not places the patient in greater danger. But excess bleeding combined with longer operating time due to poor visibility, and corrective measures required to find the appropriate placement of the pedicle screw can be disastrous. All of the above effects contribute to surgeon fatigue, which can result in increased operative complications.

What is needed is a system which will enable correct placement of a pedicle device, accurately and consistently and which will not require extensive paraspinous muscle dissection in order to obtain the required visual area for proper placement. The needed device will ideally enable a gradual graded introduction into the pedicle and give an earlier indication of problems so that any error can be quickly corrected at a time before the introduction goes any further.

Currently available surgical retractor systems fail to fulfill all of the above requirements. Consequently there is a severe need for structures and procedures to meet such requirement.

SUMMARY OF THE INVENTION

The system and method of the invention, enables a staged location and entry into the pedicle for providing insertive, progressively larger threaded fixation and superior surgical control a distance from the spine. The pedicle dart system can be used in conjunction with or without a Jamshedi trocar and sleeve, in order to give additional advantage for early focussing of the early guided location and initial placement of the pedicle dart system.

The pedicle dart system is simple and has a small number of components. These components include a guide pin, a pedicle dart fastener (preferably having some control structure for easy manual rotation) having a central opening to accommodate the guide pin, an indexed sleeve (preferably with handle) having a central opening to accommodate the threaded pedicle dart fastener to hold the dart to the sleeve. The threaded pedicle dart fastener should have a manual control surface which facilitates it axial rotation with respect to the indexed sleeve. The indexed sleeve preferably has a handle to enable rotational turning of the pedicle dart into the pedicle for ease and control.

The pedicle dart system enables use of the threaded pedicle dart fastener to both engage and disengage from an implaced pedicle dart. The indexed sleeve can impart rotational force of the sleeve directly into the pedicle dart due to the indexed connection between the pedicle dart and indexed sleeve. The threaded pedicle dart fastener is used to engaged and pull the pedicle dart to an indexed position with respect to the indexed sleeve.

The preferred method of indexing involves a pair of oppositely located fingers at the end of the indexed sleeve which are narrower than indexed slots located rearward of each of the pedicle darts. By making the fingers of the indexed sleeve narrower than the indexed slots rearward of each of the pedicle darts, the registry of the fingers of the indexed sleeve into the pedicle dart slots will occur much more rapidly. This enables easy location and re-attachment of the pedicle screw no matter whether the pedicle dart is attached away from the patient by hand or whether an implaced pedicle dart is re-attached for engagement with the pedicle dart system to remove it.

Further, the pedicle dart system also contemplates the use of the darts as starter devices to facilitate the placement of larger and higher profile conventional pedicle screws where necessary. In this limited view of the system, it can be viewed as a pedicle screw bore starter while eliminating the need to perform undue paraspinous muscle disturbance.

Moreover, as designed, one of the important aspects of the pedicle dart system involves the location of smaller fixation structures (pedicle darts) which have a lesser upward projection from the lumbar vertebra during the operation. This enables a major advance over the conventional art in which the need to place pedicle screw fixation devices before the surgical procedure often get in the way of (a) the ability to manipulate manual instrumentation to accomplish the procedure, (b) other structures used with the procedure, and (c) general visual obstruction of the surgical area.

The pedicle darts can be made in a variety of sizes, all of which can exhibit a much lower profile adjacent the surgical area. Conventional pedicle screws project high on the patient, perhaps to overcome the difficulty which would accompany conventional methods of accessing the conventional pedicle screws. The pedicle dart system provides instrumentation to reach in and re-engage otherwise hidden pedicle fixation devices. The pedicle dart system of the invention can also enable located re-attachment of larger pedicle darts or pedicle dart extensions to form the fixation needed. Conventional pedicle screws are typically single length devices having a proud, high profile because the use of conventional pedicle screws has no variability. Surgical practitioners have to fight so hard to get them in, they are reluctant to change them out and generally require a high profile. The pedicle dart system enables a level of flexibility not seen in conjunction with other fixation devices.

Further, it is not required that the darts must be able to be inserted using a thread. They can be inserted by pushing or turning, such as acting to bore into the bone using a non threaded action. Such shapes may be advantageous in removing bone in a way that will not bind or tend to put significant lateral pressure on bone tissue in the pedicle.

The use of the pedicle dart system provides a high number of significant advantages over the use of conventional pedicle screws.

1. The pedicle dart system enables the use of percutaneous technique, with the result that there is much less blood loss.
2. The pedicle dart system is completely compatible with the use of bi-planer fluoroscopy or navigational method, especially with the elongated components, allowing the insertion of the pedicle dart in a much can be precise manner.
3. The pedicle dart system enables the removal of the bulky C-arm used in conventional operations, and will therefore result in greater surgeon comfort, lessening surgeon fatigue, and therefore decreasing the possibility of surgical complications.
4. The pedicle dart system facilitates placement of a temporary pedicle dart which decreases blood loss from the hole or bore in which the pedicle dart is implaced.
5. The pedicle dart system enables the use of a low-profile pedicle dart that does not interfere with retraction blades, thus allowing for greater visibility of the surgical field.
6. The pedicle dart system enables percutaneous localization of the pedicle and insertion of the pedicle dart as a marker decreases the necessity of wide muscle stripping and therefore patient damage.
7. The pedicle dart system enables the use of a technique that allows for the preservation of the vascularity and the innervation to the longissimus muscle, which always had to previously be sacrificed using the traditional (non-pedicle dart technique). The avoidance of destruction to the longissimus muscle allows for a healthier paraspinus muscle and decreases the incidence of chronic pain associated with devascularized fibrotic paraspinous tissue.
8. Traditional placement of the conventional pedicle screw has high incidence of association with breach of the pedicular wall, which can lead to serious complications. The precision placement of the trans-pedicular path using the pedicle dart technique will minimize such complications.
9. Most important, there is a significant surgical time-saving component, as lengthy muscle dissection and direct exposure will no longer be required.
10. The shortened surgical time will mean less surgical time, providing significant cost savings for the entire health-care system.

BRIEF DESCRIPTION OF THE DRAWINGS

The invention, its configuration, construction, and operation will be best further described in the following detailed description, taken in conjunction with the accompanying drawings in which.

DETAILED DESCRIPTION OF THE PREFERRED EMBODIMENT

Figure 1:
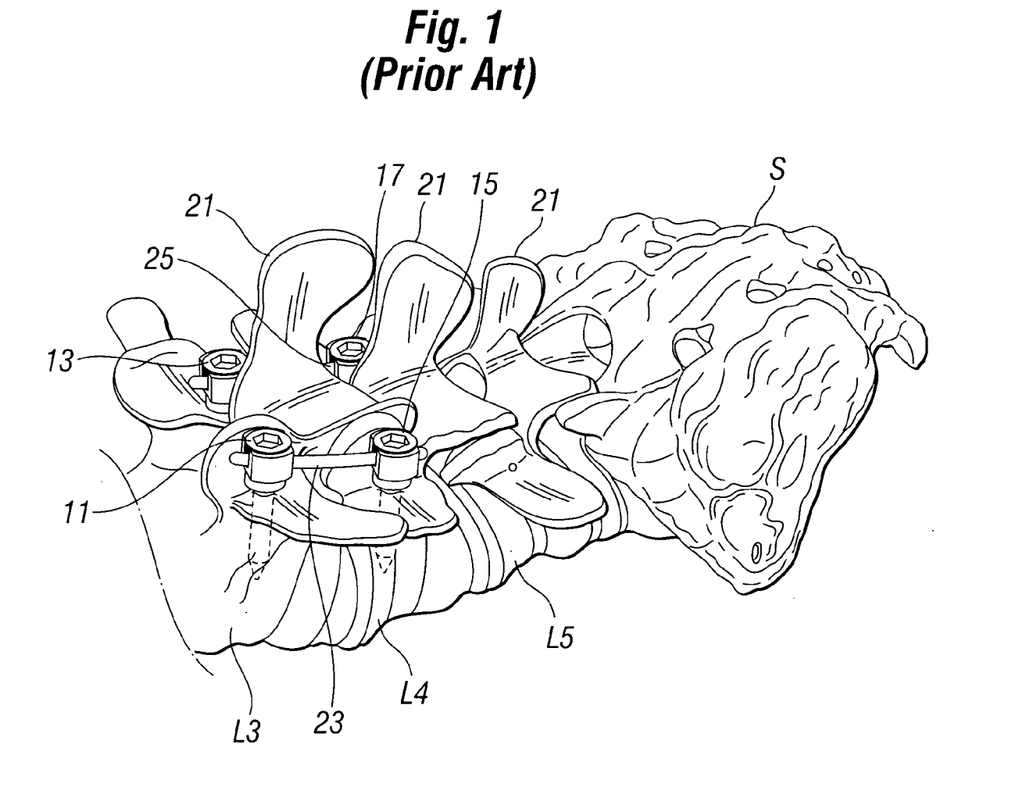
FIG. 1 is a perspective view of a prior art set of high profile conventional pedicle screws attached into the pedicles of two adjacent vertebrae and illustrating a fixation connector.

A detailed description of the preferred embodiment will be best begun by examining a perspective view of the lower lumbar vertebrae L3, L4, L5 and sacrum S shown in perspective in FIG. 1. In operative procedures in which work is to be done between two adjacent vertebrae, those two vertebrae must be fixed and held apart so that the space between those vertebrae is maintained. Traditionally this has been done by using conventional pedicle screws 11, 13, 15 and 17 seen in FIG. 1. The conventional pedicle screws 11, 13, 15 and 17 engage significant bone mass by placement through the pedicle structure of each vertebra into which they are placed. In the three dimensional view of FIG. 1, the conventional pedicle screws 11, 13, 15 and 17 seem to have an open placement, during an actual surgical procedure on a patient, the pedicle screws 11, 13, 15 and 17 must be located through and despite significant layers of muscular tissue.

As previously discussed, dissection of the muscles surrounding the spiny process 21 of each of the vertebrae will damage the patient, permanently weaken the back and can delay or completely prohibit patient recovery. It is noted that the conventional pedicle screws 11, 13, 15 and 17 have a high profile, so high as to cause a similarly high engagement of an interconnect member 23 between conventional pedicle screws 11 and 15 and an interconnect member 25 between conventional pedicle screws 13 and 17. The use of two such interconnect members 23 and 25 act to bilaterally stabilize the adjacent vertebrae (in this case L3 and L4) in a position as they were located prior to the surgical procedure. In the case of disc removal and implant placement it is advantageous to have the two vertebra stabilized in a natural position so that implant selection and placement into a proper space can be facilitated.

However, the use of the conventional pedicle screws 11, 13, 15 and 17 of FIG. 1, along with the interconnect members 23 and 25 create a significant interfering structure which can block access to the intervertebral space, and also can physically interfere with any retractor system used to facilitate access to the intervertebral space. Retractor systems which operate more closely to the spine are more stable and subject to greater control by the surgical practitioner. Further, when retractor system is closer to the patient, a wider view is available, all other factors remaining the same.

FIG. 1 also illustrates that the conventional pedicle screws 11, 13, 15 and 17 have to have an insertion point and angle which will enable the conventional linear pedicle screw to travel straight through the pedicle and into the main vertebra body. This must be accomplished with minimum damage to bone tissue, and without angling into the spine, and without simply missing its path so that it emerges from the pedicle even if it continues back into the vertebra. Any opportunity to fail to fully engage bone volume results in a probability that the conventional pedicle screws 11, 13, 15 and 17 will not hold and may fail in their contribution to fix the interconnect members 23 and 25.

When it is considered that the large amounts of tissue must be removed or compromised to give the surgical practitioner the ability to locate the exact point of insertion and then to rotatably insert the conventional pedicle screws 11, 13, 15 and 17 at the correct angle, it can readily be seen that conventional pedicle screw insertion is both difficult and fraught with the possibility of error, times four. Further, because the conventional pedicle screws 11, 13, 15 and 17 have relative large diameter compared to the pedicle, the room for error which would still allow a successful insertion is reduced.

Figure 2:
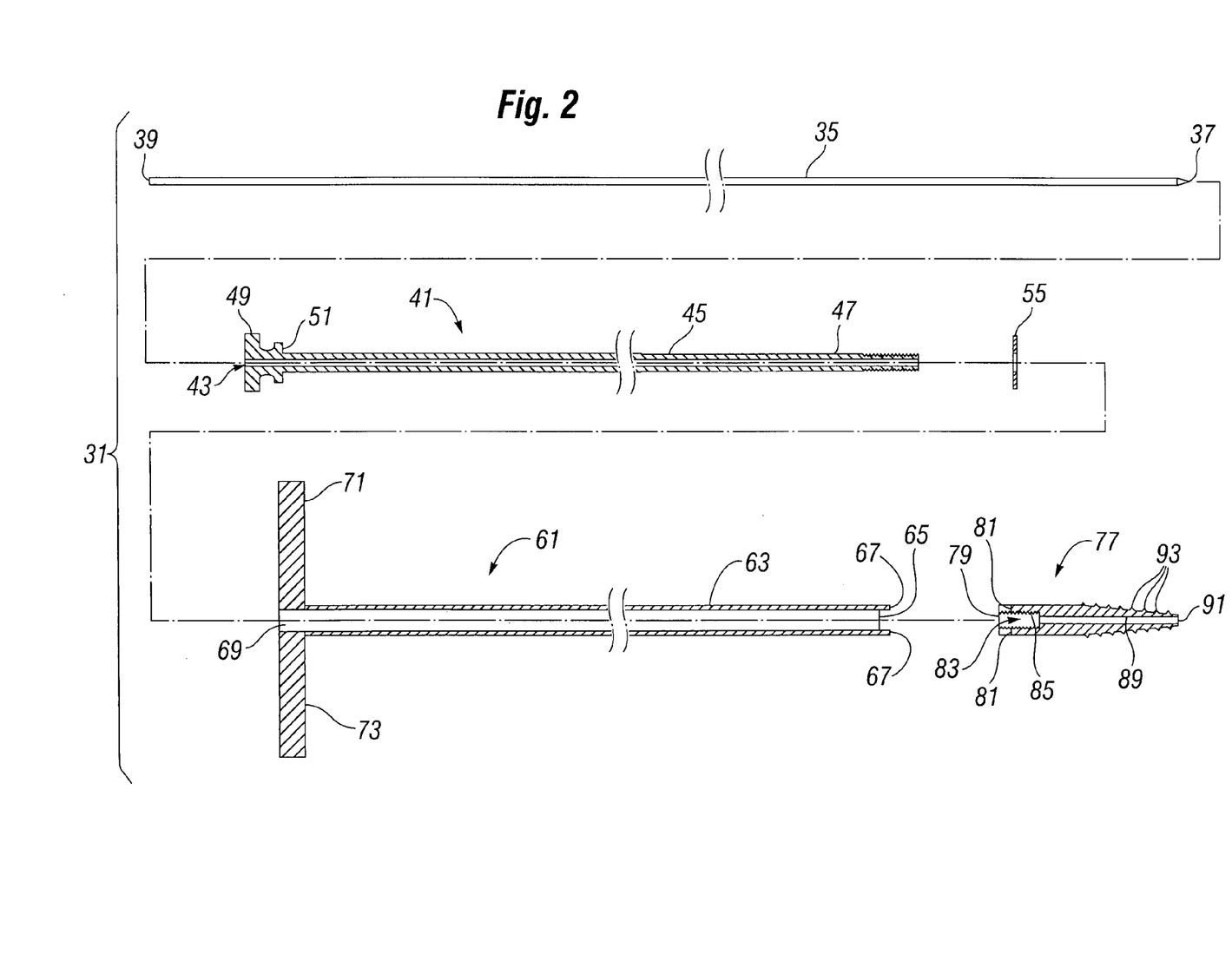
FIG. 2 is a sectional exploded view illustrating the basic components in a pedicle dart system.

Referring to FIG. 2, an exploded view of a pedicle dart system 31 is illustrated. A guide pin 35 is preferably a solid length of material having a sharp point 37 at one end opposite a blunt end 39. A pedicle dart fastener 41 includes a guide pin through bore 43 for enabling the guide pin 35 to easily pass through as well as to rotate. The pedicle dart fastener 41 in the embodiment shown as a main barrel 45 and a set of external threads at one end. The opposite end has an enlarged control knob 49 spaced apart from an insertion limiting land 51 to insure that the enlarged control knob 49 will be prominent and easily actuatable with regard to any type of instrumentation into which the pedicle dart fastener 41 is inserted.

It is understood that the use of external threads 47 to rotationally engage a pedicle dart (to be discussed) by threadable rotation to achieve attachment and axial movement, is but one of many ways this can be accomplished. Other ways include a quick key insertion, an external snap detent, or magnetic attraction or any other structure. The remainder of the structure will reveal that the external threads 47 will not undergo a static turning force and therefore no rotational pressure will be exerted on the external threads 47.

An optional friction washer 55 is seen for eliminating component wear and its need will depend upon the materials chosen for the pedicle dart system. Next is seen the indexed sleeve 61. Indexed sleeve 61 includes a main cylindrical barrel 63 having a terminal end 65 with a pair of fingers 67 extending beyond the terminal end 65. The indexed sleeve 61 has a central bore 69 through which the main barrel 45 of the pedicle dart fastener 41 may freely pass and rotate. A pair of handles 71 and 73 extend away from the end of the indexed sleeve 61 to facilitate manual rotation of the indexed sleeve 61 with some level of manual force.

To the right of the indexed sleeve 61, a pedicle dart 77 is shown in cross section. As will be seen, although the pedicle dart 77 can have a variety of functional structures, the pedicle dart 77 shown in FIG. 2 has a threaded conical exterior and internally threaded surfaces.

Beginning at the left, the pedicle dart 77 has a pair of fingers 79, only one of which is seen due to the cross sectional nature of the drawing. The fingers 79 of the pedicle dart 77 interlock with the fingers 67 of the indexed sleeve 41 and will ideally extend all the way to the terminal end of the indexed sleeve. An end 81 of the pedicle dart 77 defines the point that the pedicle dart 77 fingers 79 extend rearwardly of it. The ends 81 accommodate the terminal ends of the fingers 67 of the indexed sleeve 41 extending toward the pedicle dart 77 to rotationally engage it.

Pedicle dart 77 has a bore 83 having an internal threaded surface 85 which is complementary to the threaded surface 57 of the pedicle dart fastener 41. Beyond the internal threaded surface 85, the pedicle dart 77 has a guide pin bore 89 which extends through the pedicle dart 77 and opens at a tip end 91 of the pedicle dart 77. As can be seen, when the pedicle dart 77 is brought close to the end 65 of the indexed sleeve 61 such that the fingers 67 of the indexed sleeve slide past the fingers 79 of the pedicle dart 77, any rotational force applied to the indexed sleeve will be transmitted to the pedicle dart 77. Pedicle dart 77 is also seen as having an externally threaded surface 93 for boring into bone tissue. A spiral cutting thread can be used, but also other non-spiral cutting surfaces, such as a ribbed cone with tapered radiating relatively angled members for an even bore, or a conical rasp.

So long as the pedicle dart 77 is in close relationship with the indexed sleeve 61, the fingers 67 and 79 will directly transfer any turning or movement of the indexed sleeve 61 through to the pedicle dart 77. In essence, the indexed sleeve 61 becomes a long device which can have its tip member selectively attached or removed. The pedicle dart fastener 41 serves several. First it can engage or disengage the pedicle dart 77. Secondly, it can pull the pedicle dart 77 closer enough to the indexed sleeve 61 that the fingers 67 and 79 will engage each other. Third, it keeps the pedicle dart 77 and index sleeve centered to insure that the engagement of the fingers 67 and 79 are even and both rotate fully engaged around a common axis.

FIG. 2 illustrates that the guide pin 35 can be freely inserted into the guide pin bore 43 at any time and from either end of the guide pin bore 43. The guide pin 35 can be used independently with the combination pedicle dart 77, indexed sleeve 61 and main cylindrical barrel 63 assembled as a unit. In other words, the guide pin 35 can be inserted either by gentle force or by gentle tapping to locate a point of insertion. The guide pin 35 is used as an easy-to-handle, long object which can be oriented to indicate the angle at which the pedicle dart 77 is to be inserted. Then, the combination pedicle dart 77, indexed sleeve 61 and main cylindrical barrel 63 assembled as a unit can be guided over the blunt end 39 of the guide pin 35 and then slid along the guide pin directly to the exterior of the pedicle. A few turns of the combination of the pedicle dart 77, indexed sleeve 61 and main cylindrical barrel 63 assembled as a unit will result in some of the externally threaded surface beginning to engage the bone tissue of the pedicle. Once insertion of the pedicle dart 77 begins, the guide pin 35 can be withdrawn while the remainder of the pedicle dart system 31 is turned to put the pedicle dart 77 fully into the bone tissue.

Once the pedicle dart 77 is fully inserted, the surgical practitioner can manually turn the enlarged control knob 49 in a direction that will back the set of external threads 47 of the main barrel 45 out of the threaded surface 85 of the pedicle dart 77. This action enables the pedicle dart 77 to begin to move forward with respect to the indexed sleeve 61 to enable the fingers 67 of the main cylindrical barrel 63 to disengaged from the pair of fingers 79 of the pedicle dart 77. Further turning of the enlarged control knob 49 enables the pedicle dart fastener 41 to become completely disengaged from the pedicle dart 77.

The same process can be followed in reverse to re-engage the pedicle dart 77. The combination of the indexed sleeve 61 and main cylindrical barrel 63 assembled as a unit with the indexed sleeve 61 urged forward will cause the set of external threads 47 of the indexed sleeve 61 to protrude forward of the fingers 67 and in a position to find and engage the internal threaded surface 85 of a pedicle dart 77. Turning the enlarged control knob 49 in a direction that will begin to engage the set of external threads 47 of the pedicle dart fastener 41 into threaded surface 85 of the pedicle dart 77 will begin to draw the pedicle dart 77 toward the indexed sleeve 61. Slight turning of the indexed sleeve 61 will cause the fingers 67 to assume a complementary position with respect to the fingers 79 of the pedicle dart 77, with fingers 67 and 79 sliding past each other to enable rotational re-engagement of the indexed sleeve 61 with the pedicle dart 77. This same procedure is used for both loading a new pedicle dart 77 by hand and for re-engaging a pedicle dart 77 which may have previously been implaced in bony tissue. In the latter case, once re-engaged, the indexed sleeve 61 can be used to extract the pedicle dart 77. The technique of extraction will depend upon the type of pedicle dart 77, as will be shown. Where the externally threaded surface 93 is present, turning to loosen the threads of the externally threaded surface 93 sufficient to disengage such externally threaded surface 93 will precede simple extraction.

Figure 3:
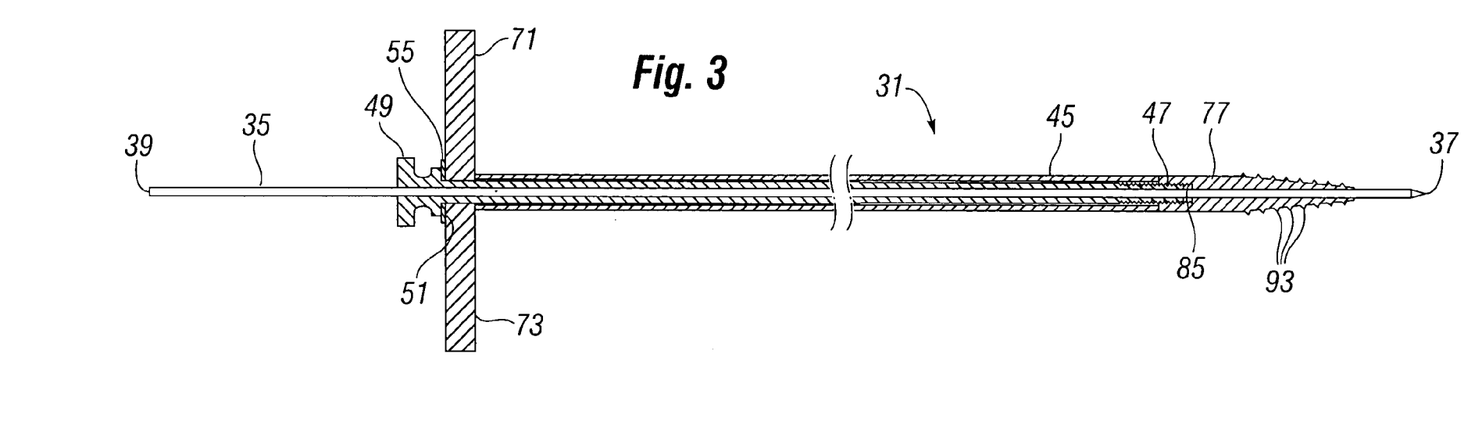
FIG. 3 is a sectional assembled view illustrating the interfitted components of the basic pedicle dart system.

Referring to FIG. 3, a sectional view illustrating the assembled pedicle dart system 31 is seen. The guide pin 35 is preferably much longer than the pedicle dart fastener 41 so that a sufficient length of the guide pin 35 will be available for easy manipulation. The pedicle dart fastener 41 can be withdrawn back through the main barrel 45 of the indexed sleeve 61 main cylindrical barrel 63, and an optional structure can be present to stabilize the pedicle dart fastener 41 longitudinally with respect to the main barrel 45 of the indexed sleeve 61. Such optional structure may include a set screw extending through the main barrel 45 of the indexed sleeve 61 to engage a reduced land on the pedicle dart fastener 41, or some other spring detent can be used. Any optional structure should be configured with a mind toward facilitating sterilization of this instrument.

Figure 4:
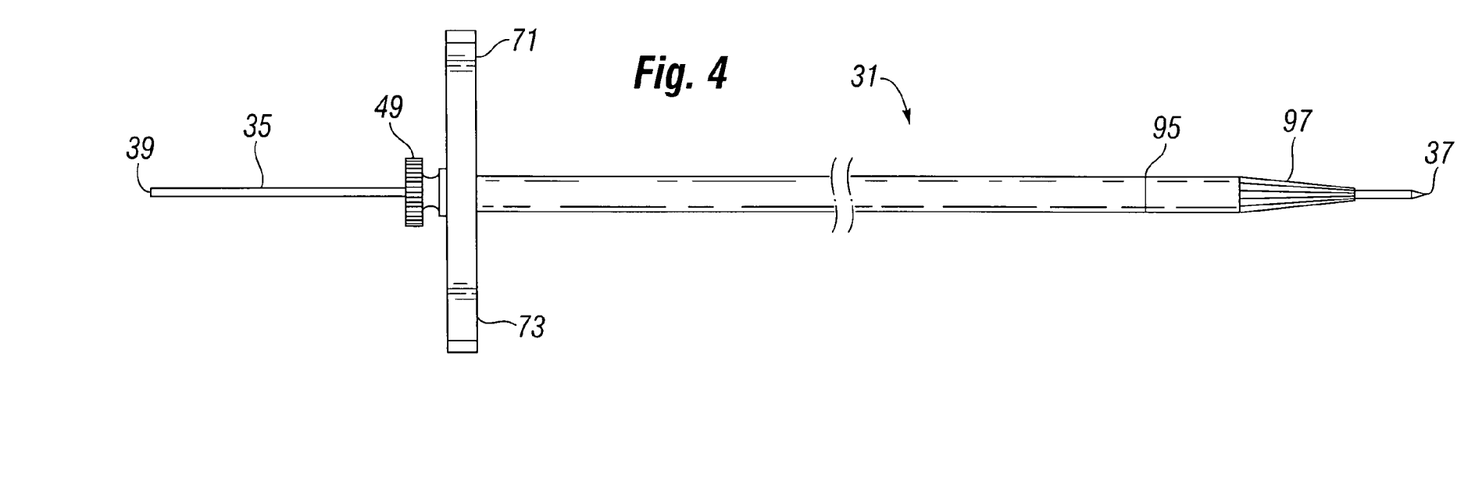
FIG. 4 is a plan assembled view illustrating the interfitted components of the basic pedicle dart system with a further embodiment of a pedicle dart having conically tapering exterior ribs.

FIG. 4 is a plan assembled view illustrating the interfitted components of the basic pedicle dart system 31 with a further embodiment of a pedicle dart seen as pedicle dart 95. Pedicle dart 85 has conically tapering exterior ribs 97 and illustrates that the pedicle dart system 31 is not limited to an externally threaded entry into bone tissue. The conically tapering exterior ribs of pedicle dart 95 will enable more of a concentrically even wearing effect by which bone entry is accomplished. This also reduces the possibility that the adjacent tissues might be overly compressed from the action of externally threaded surface 93 combined with forward pressure applied by a surgical practitioner. In effect, the surgical practitioner can select the particular pedicle dart 77 or 95 desired for use given the bone tissue conditions.

Figure 5:
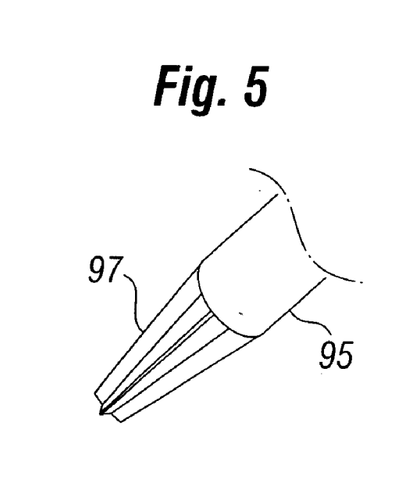
FIG. 5 is an expanded perspective view of the pedicle dart seen in FIG. 4 illustrating the taper and ribs.
Figure 6:
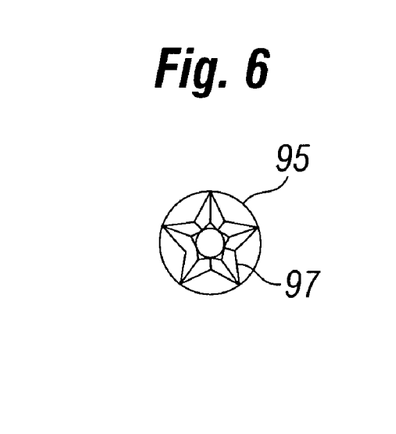
FIG. 6 is an end view of the pedicle dart of FIGS. 4 and 5 illustrating the geometric shape as having deep ribs, which are five in number.

Referring to FIG. 5, an expanded perspective view of a portion of the pedicle dart 95 is seen in a position below the terminal end 65 and pair of fingers 67 seen in previous figures. The relatively deep tapered rib section 97 is seen. Referring to FIG. 6, an end view of the pedicle dart of FIGS. 4 and 5 illustrates the geometric shape as having deep ribs, which are seen to be five in number.

Figure 7:
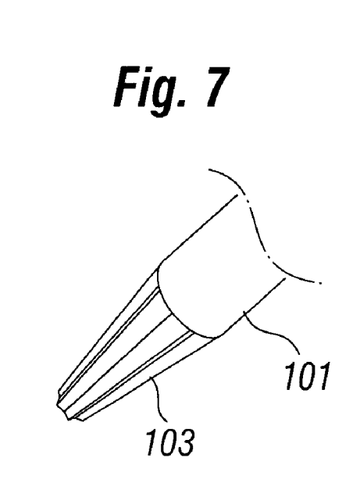
FIG. 7 is an expanded perspective view of a further embodiment of the pedicle dart as having a taper, but with more shallowly formed and more numerous ribs.
Figure 8:
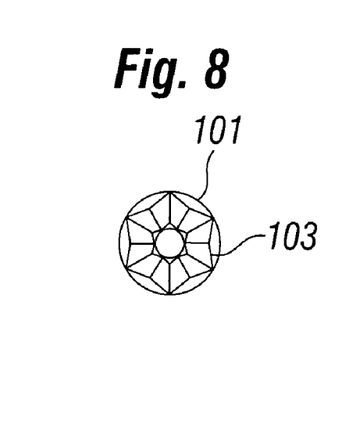
FIG. 8 is an end view of the pedicle dart of FIG. 7 illustrating the geometric shape as having shallow ribs, which are six in number.

Referring to FIG. 7, an expanded perspective view of a further embodiment of a pedicle dart 101 as having a tapered rib section 103, but with more shallowly formed and more numerous ribs. Referring to FIG. 8, an end view of the pedicle dart 101 of FIG. 7 illustrating the geometric shape as having shallow ribs within its tapered rib section 103, which are six in number.

Figure 9:
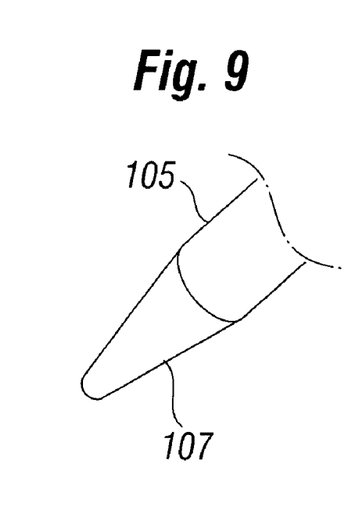
FIG. 9 is an expanded perspective view of a further embodiment of the pedicle dart as having a conical taper.
Figure 10:
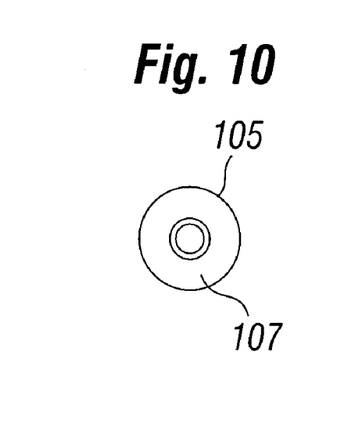
FIG. 10 is an end view of the pedicle dart of FIG. 9 illustrating the geometric conical shape.

Referring to FIG. 9, an expanded perspective view of a further embodiment of the pedicle dart is seen as a pedicle dart 105 as having a conical taper 107. This embodiment can be used where the bone tissue is soft or where the surgical practitioner wants only a small or force determined opening or starter aperture in the bone tissue. Referring to FIG. 10, an end view of the pedicle dart 105 of FIG. 9 illustrating the geometric conical shape taper 107.

Figure 11:
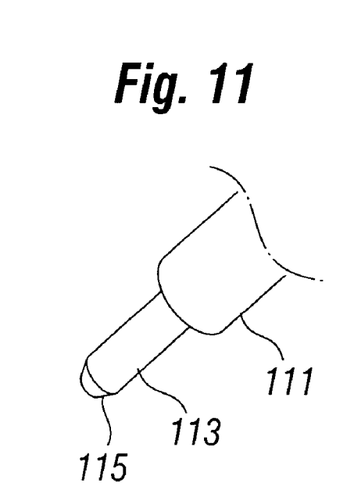
FIG. 11 is an expanded perspective view of a further embodiment of a pedicle dart formed as a probe having a reduced diameter portion with an optional slight small end conical taper.
Figure 12:
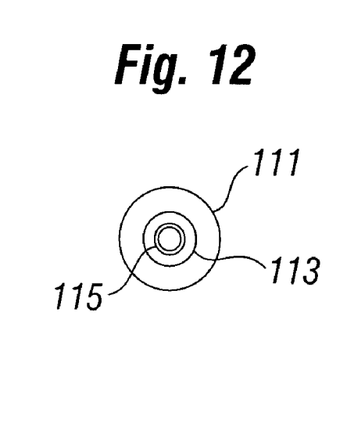
FIG. 12 is an end view of the pedicle dart of FIG. 11 illustrating the geometric stepped shape.

Referring to FIG. 11 an expanded perspective view of a further embodiment of a pedicle dart 111 formed as a probe having a reduced diameter portion 113 with an optional slight small end conical taper 115. The pedicle dart 111 is especially useful with an indexed sleeve 61 used as a probe to move tissues and "feel", in addition to looking for pedicle placement. Thereafter the guide pin 35 can be employed to make an impression on the spot on the pedicle where further activity is to occur. In that case, the assembly including the indexed sleeve 61, pedicle dart fastener 41 and pedicle dart 111 can be removed from the guide pin 25, then loaded with pedicle darts 105, 95, 101 or 77 and then re-inserted over the guide pin 35 for further pedicle dart insertion activity. Referring to FIG. 12, an end view of the pedicle dart 105 of FIG. 11 is shown and illustrating the geometric stepped shape.

Figure 13:
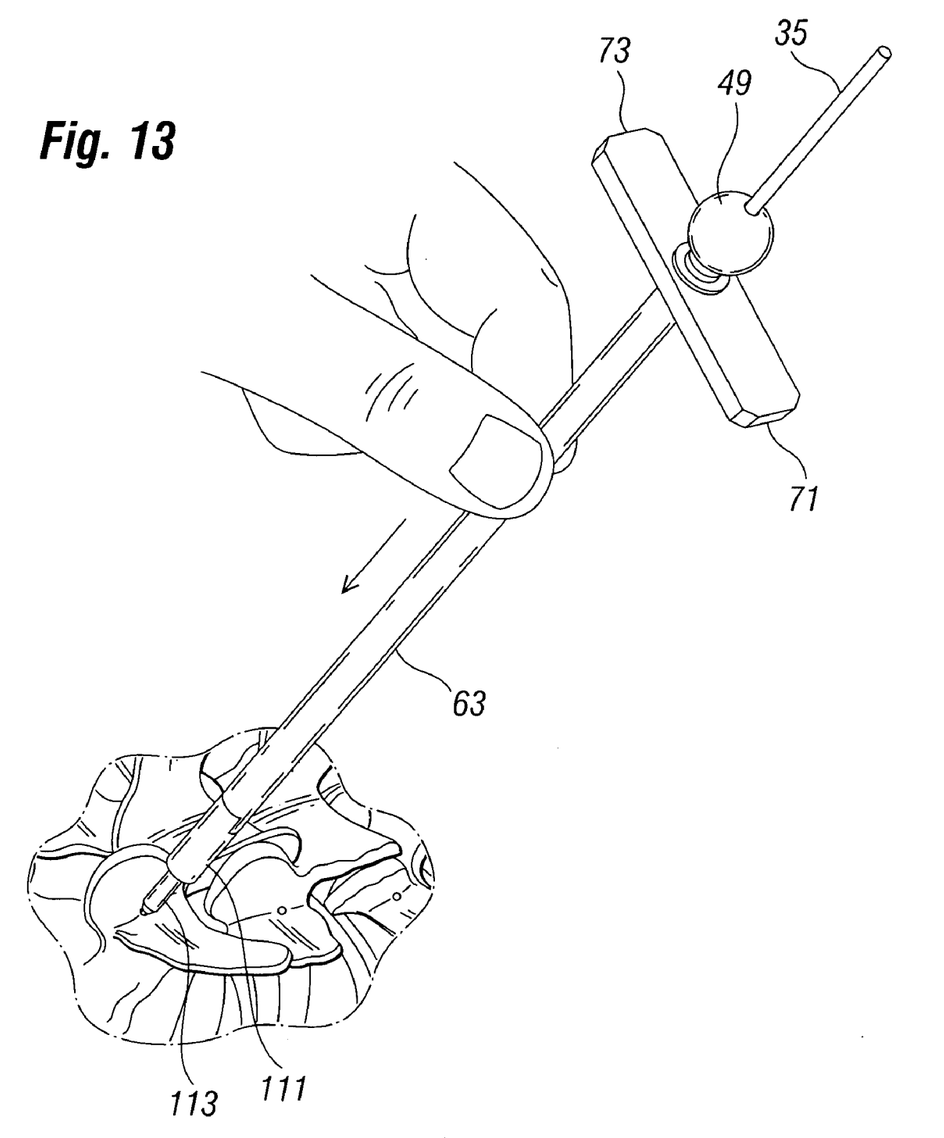
FIG. 13 illustrates the pedicle dart system configured as a probe and using the probe pedicle dart seen in FIGS. 11 and 12 with the guide pin withdrawn while using it as a probe to locate the point where the guide pin is to be inserted.

FIG. 13 illustrates the pedicle dart system configured as a probe and using the probe pedicle dart 111 seen in FIGS. 11 and 12 with the guide pin 35 withdrawn while using it as a probe to locate the point where the guide pin 35 is to be inserted. Also illustrated is a slightly differently shaped enlarged control knob 49 as having a more spherical appearance.

Figures 14, 15:
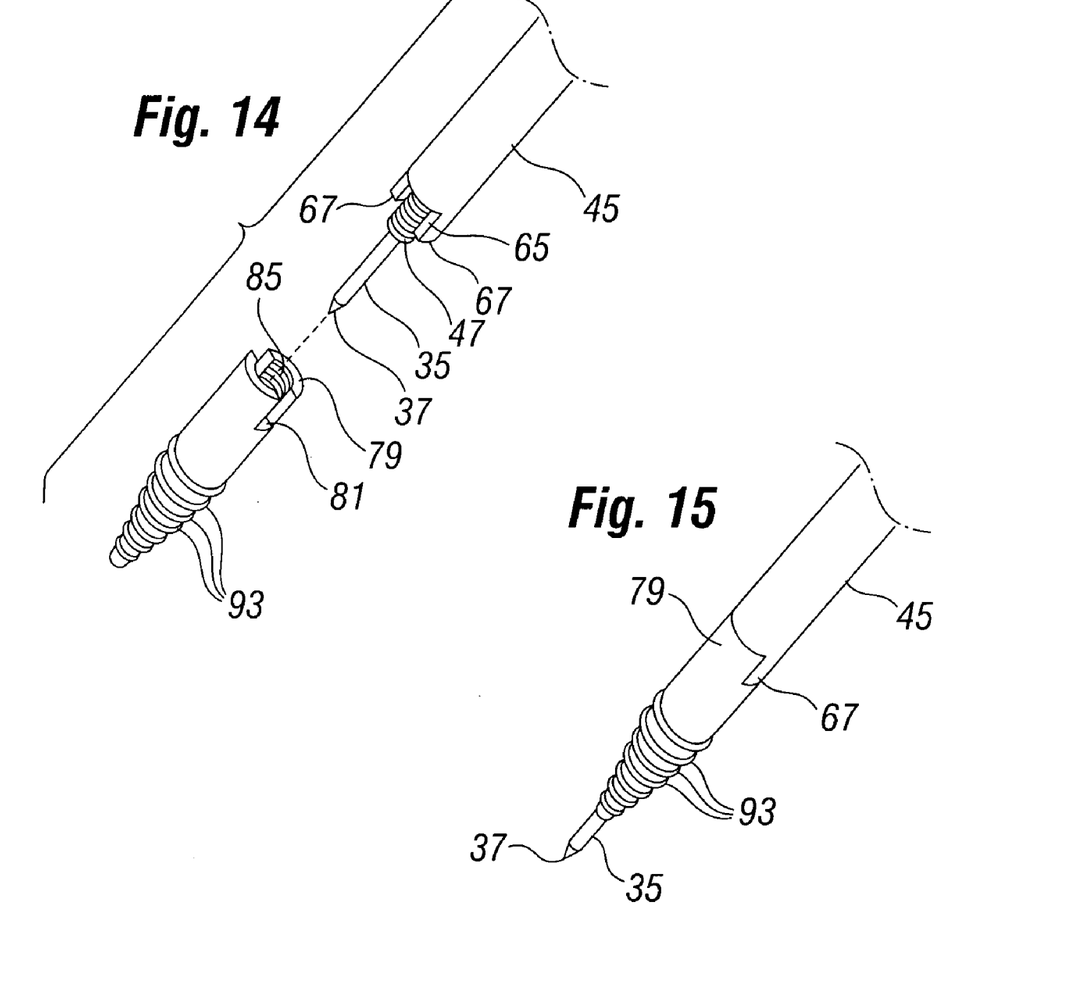
FIG. 14 illustrates a perspective view of the pedicle dart of FIGS. 2 and 3 in a position to be loaded onto the end of the pedicle dart fastener and indexed sleeve.
FIG. 15 illustrates a perspective view of the components seen in FIG. 14 but joined to form a complete pedicle dart system assembly ready for guide pin guided implacement.

Referring to FIG. 14, a perspective view of the pedicle dart 77 of FIGS. 2 and 3 is shown in a position to be loaded onto the end of the pedicle dart fastener, of which only the tip end having threads 47 is seen, and in which the guide pin 35 is optionally present to aid in alignment. Guide pin 35 is not required for attachment of the pedicle dart 77 but guide pin 35 insertion will automatically concentrically align the pedicle dart 77 so that the only other alignment is rotational, to align the fingers 79 with fingers 67. Fingers 79 are seen as optionally having a greater radial extent while the fingers 67 have a lesser radial extent, but this need not be the case. Further, instead of using two fingers on each component (pedicle dart 77 and the end of the main barrel 45), one finger, three fingers, or four or more fingers could be used. Note that the threaded surface 47 of the end of pedicle dart fastener 41 extends slightly beyond the most distal ends of the fingers 67 so that the internal threaded surface of the pedicle dart 77 may be engaged before the fingers 67 and fingers 79 need be rotated out of any interfering alignment.

Referring to FIG. 15, a perspective view of the components seen in FIG. 14 are shown as joined to form a complete pedicle dart system 31 assembly ready for guide pin 35 guided implacement.

Figure 16:
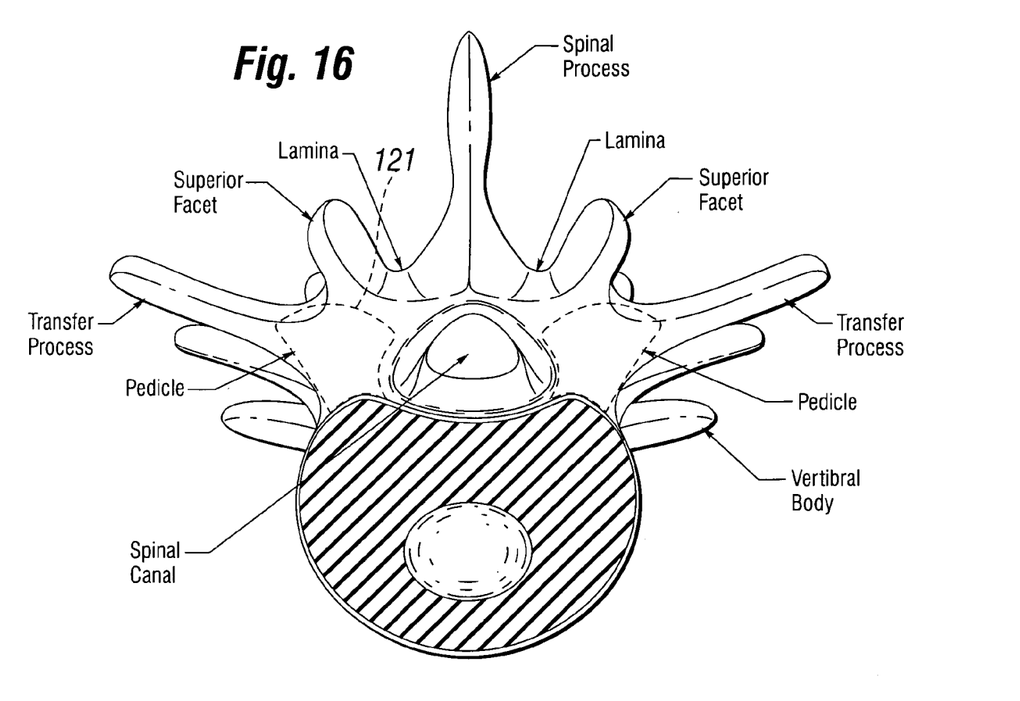
FIG. 16 illustrates a partial sectional view of a vertebra with identification of component parts and with the pedicle shown in dashed line format behind the transfer process.
Figure 17:
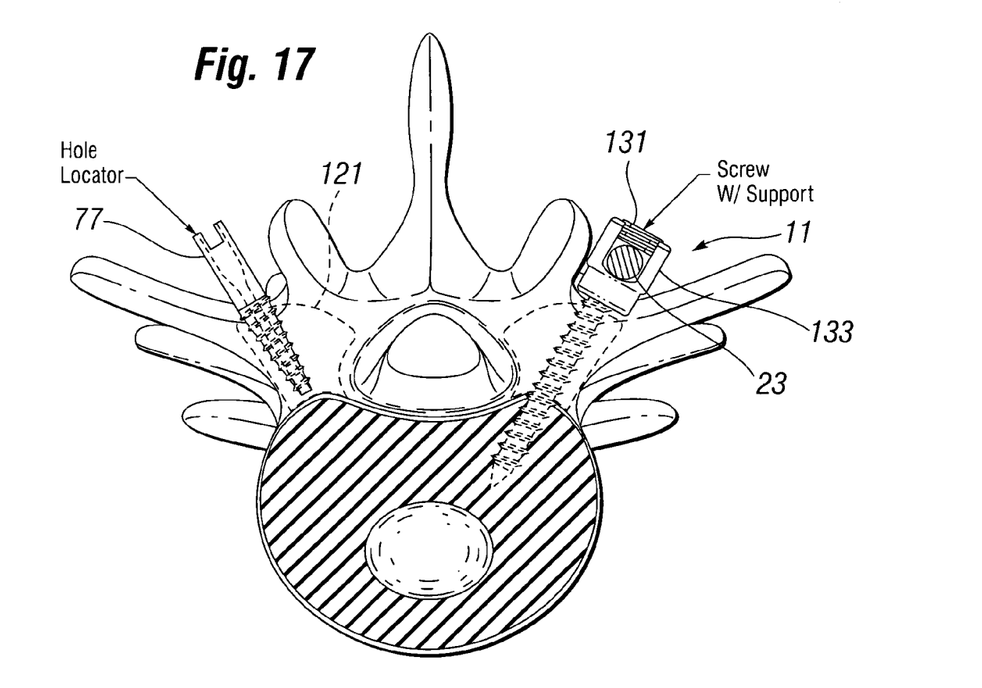
FIG. 17 illustrates insertion of a pedicle dart in comparison with the pedicle screw seen in FIG. 1 and can be used to illustrate several aspects of the differences and possibilities for cooperation between the two structures.

Referring to FIG. 16, a partial sectional view of a vertebra with identification of component parts and with the pedicle 121 shown in dashed line format behind the transfer process is given for further reference. Referring to FIG. 17, an illustration of insertion of a pedicle dart 77 is shown in comparison with the conventional pedicle screw 11 seen in FIG. 1 and can be used to illustrate several aspects of the differences and possibilities for cooperation between the two structures. The conventional pedicle screw 11 is also seen has having a compression screw 131 which operates within a housing 133 to compress the interconnect member 23.

First, it can be noted that the pedicle dart 77 is smaller and shorter than the conventional pedicle screw 11. The pedicle dart 77 is shown in a location where it has been only half way inserted into the pedicle. It can be inserted further in or less further in. Conventional pedicle screw 11 is seen as having a proud high appearance. With the conventional pedicle screw 11 the surgical view is obstructed in terms of height. The pedicle dart 77 however can go deeper into the bony mass to have a low profile appearance which interferes less with other surgical instrumentation and structures and yet still marks the angle and location. Further, the internal threaded surface 85 of the pedicle dart 77 (not seen in FIG. 17) which is used to engage set of external threads 47, can similarly be used to anchor other interconnect structure used during the operation where permissible.

However, one of the main purposes for the pedicle dart is to more easily "start" the path into the bone tissue, for both angle and location. In many operations the pedicle darts 77 may be implaced for only 30 minutes before either being removed or supplemented by other different sized structures threadably or otherwise inserted into the bone tissue, especially where greater depth, greater diameter, or other characteristics are desired. Other different sized structures may be expected to be inserted and removed by virtue of their compatibility with the pedicle dart system 31 of the invention.

Figure 18:
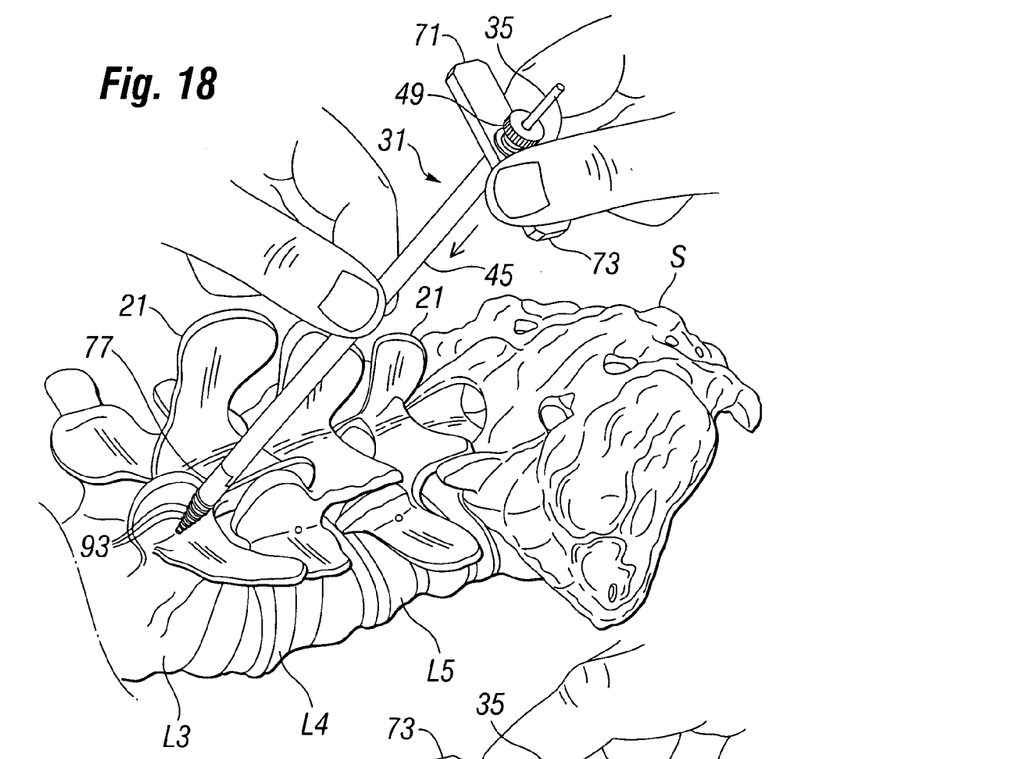
FIG. 18 is a perspective view illustrating the initial step of guide pin location and at the point in the process where the pedicle dart has translated along the guide pin and first makes contact with the pedicle.

Referring to FIG. 18. a perspective view is used to illustrate the initial step of initial contact of the pedicle dart 77 with the pedicle dart system 31 at a point in time after the guide pin 35 has used, with or without the probe configuration seen in FIG. 13, for marking location where the pedicle dart is to be inserted. It is at this time that the surgical practitioner angularly orients the pedicle dart system 31 so that further manipulation of the pedicle dart system will result in the linear entry path desired. The pedicle dart 77 is shown as being securely attached so that rotation of the indexed sleeve will result in rotation of the pedicle dart 77. The view illustrates a time just before the rotation of the components of the pedicle dart system 31 begins, with the combination pedicle dart fastener 41, indexed sleeve 61, and pedicle dart 77 translated along the guide pin 35 first making contact with the pedicle 121.

Figure 19:
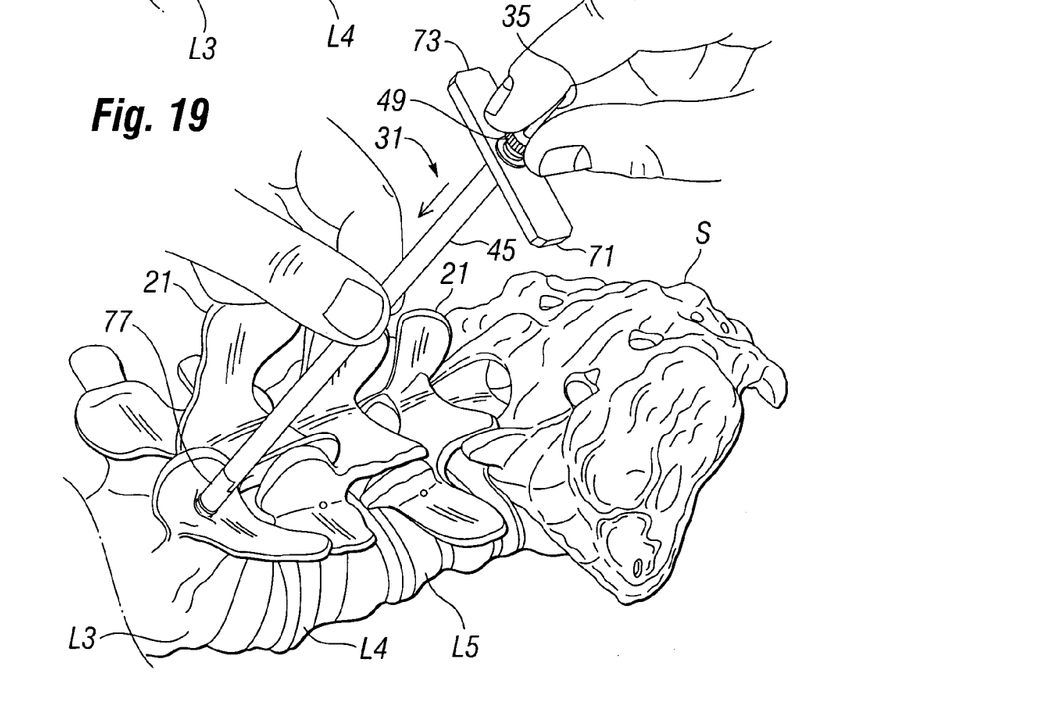
FIG. 19 is a view similar to that seen in FIG. 18 in which the pedicle dart has been inserted and at the point where the surgical user is just about to begin turning the control knob of the pedicle dart fastener to release the pedicle dart.

Referring to FIG. 19 is a view similar to that seen in FIG. 18 in which the pedicle dart has been inserted to a depth of about half of its length and at the point where the surgical user is just about to begin turning the control knob 49 of the pedicle dart fastener 41 to release the pedicle dart 77 and just after the turning operation has ceased.

Figure 20:
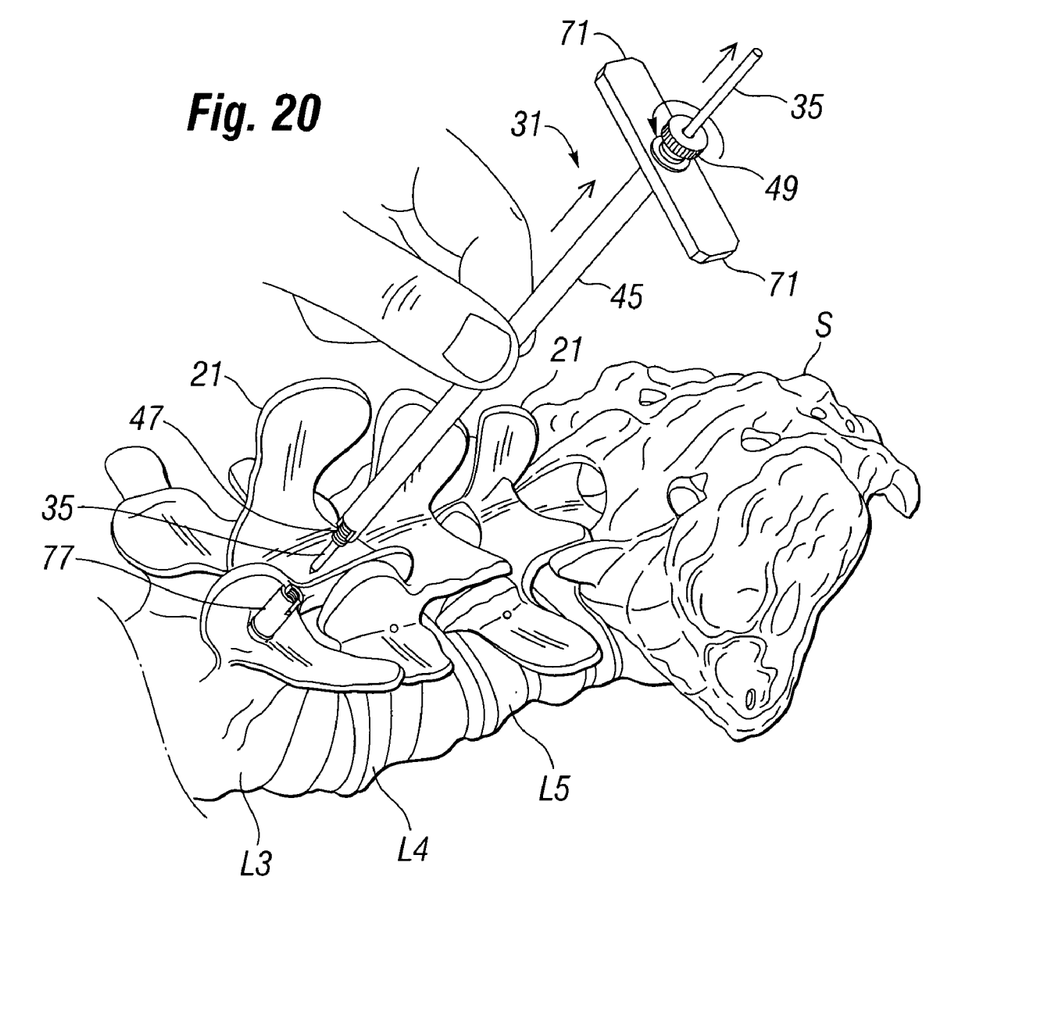
FIG. 20 is a view similar to that seen in FIGS. 18 and 19 in which the indexed sleeve and pedicle dart fastener has been decoupled from the pedicle dart and is being moved away from the surgical field.

Referring to FIG. 20, a view similar to that seen in FIGS. 18 and 19 is shown in which the indexed sleeve 61 and pedicle dart fastener 41 has been decoupled from the pedicle dart 77 and is being moved away from the surgical field. The practitioner would repeat the process of FIGS. 18-20 to insert as many pedicle darts as necessary. Ideally, the pedicle dart may be a tapered, cylindrical device having a sharp point at one end leading to self-tapping threads 93 on the outer surface for approximately 75% of its length. The opposite end is flat, and may be male or female indexed to match the female or male index, respectively on the indexed sleeve 61. The center of the pedicle dart 77 may be cannulated to accept the guide pin 35.

It is clear that the pedicle dart system of the invention can be modified to handle a wide variety of Procedures. The material used for all components of the pedicle dart system should be capable of withstanding sterilization and impact. Different materials may be employed based upon the forces and interconnection forces expected to be encountered. Although the pedicle dart system 31 can be used in many different types of surgical procedures, an example involving minimally invasive surgery transforaminal lumbar interbody fusion (MIS TLIF) will be described as one of those examples.

MIS TLIF Procedure

1. Insert any guide pin to identify the level of the lumbar disk to be removed.
2. Make a midline incision centered over the guide pin 35 appropriate for the levels of surgery to be performed, which is usually the distance from the tip of the spinous process of the levels to be fused.
3. Undermine the full thickness of the skin 2-3 cm circumferentially to allow the incision to be moved in all directions.
4. Make a fascial incision 1-2 cm lateral to the spinous processes. Insert Cobb elevator and sweep the multifidus muscle off the spinous processes and lamina and lateral to the facet joint. Insert MIS retractor with the proper blade length and shape and open the retractor blades to retract the soft tissue from the interlaminar space. The inverted "V"-shaped space thus created allows for excellent visualization for the laminectomy/diskectomy.
5. Fasten the retractor to the universal arm attached to the surgical table to stabilize the retractor if desired.
6. Perform a facetectomy if TLIF procedure is to be performed. Take precaution not to injure the exiting root cephalad to the disk and use a dural retractor to retract the dura and traversing root medially.
7. Perform a complete diskectomy. Prepare the disk space and insert the inter body cage of choice. A more lateral Wiltse approach to be described next can be used for inserting a longer "banana" TLIF cage for safer insertion.

8. Remove the MIS retractor and make another longitudinal fascial incision on the lateral border of the Longissimus muscle. The location of this fascial incision can also be determined by the location of the pedicle darts 105, 95, 101 or 77 as visualized with the C-arm. Insert a Cobb elevator to sweep the muscle off of the transverse processes and lateral facet joints. Insert the MIS retractor of the appropriate blade length and open the retractor blades sufficient to visualize the operative area of interest. If the fascial incision appears to be too lateral, the fascial incision can be made more medially and a "true" Wiltse muscle-splitting approach can be utilized. Deploy the retractor blades cephalad-caudally. Medial/lateral retraction may be necessary. On the medial side, a hook retractor should be used, and laterally, a blade retractor would be more effective to retract the muscle.

9. Following placement of the TLIF cage, the proud head of the pedicle dart 105, 95, 101 or 77, can be engaged easily due to the indexed sleeve 61. Remove the pedicle dart 105, 95, 101 or 77. The appropriate conventional pedicle screw can then be inserted through the hole prepared by the pedicle dart, and the contoured rod can then be applied to the heads of the conventional pedicle screw. The construct can then be compressed, and the locking screws tightened over the rod. The MIS retractor is then removed.

Internal Fixation of the Opposite Side

1. Move the midline incision to the opposite side.
2. Make a longitudinal fascial incision on the opposite side to begin the Wiltse approach. Using muscle-sparing technique, strip the muscle attachments on the transverse processes. Insert the MIS retractor with the appropriate length retractor blades, and then open the blades Cephalad-Caudally to expose the heads of the pedicle dart 105, 95, 101 or 77. Deploy medial/lateral retractor as required for sufficient exposure. Decorticate the transverse processes and lateral surface of the facet joint. Remove the pedicle dart as described before and replace with the final conventional pedicle screw 11. Insert the appropriate interconnect member 23 into the conventional pedicle screw head housing 133; then compress and tighten the locking screws 131. Apply bone graft to the decorticated postero-lateral gutter, then remove MIS retractor. Suture the fascial incisions with appropriate suture material of choice and close the wound in the usual fashion.

While the present system has been described in terms of a system which includes instrumentation, procedures and wide range of purposes to facilitate a difficult surgical task, one skilled in the art will realize that the structure and techniques of the present system can be applied to many instruments, including any instrument which has the ability to transmit high torque, selective attachment and detachment, and which accentuates the location and angle of approach of an entry into any point in the human body.

Although the system of the invention has been derived with reference to particular illustrative embodiments thereof, many changes and modifications of the systems shown may become apparent to those skilled in the art without departing from the spirit and scope of the inventive system. Therefore, included within the patent warranted hereon are all such changes and modifications as may reasonably and properly be included within the scope of this contribution to the art.

What is claimed:

1. A pedicle dart system comprising:
   a guide pin having a first pointed end and a second end opposite the first end;
   a pedicle dart fastener having a manual actuation knob at a first end and a set of external threads at a second end, the pedicle dart fastener having a first guide pin through bore sized to freely enable the guide pin to axially pass therethrough;
   an indexed sleeve having a handle end and a first indexed end, and having a central bore through which the pedicle dart fastener may freely pass limited only by the manual actuation knob of the pedicle dart fastener;
   a pedicle dart having a first tip end and a second indexed end for engaging the first indexed end of the indexed sleeve, the pedicle dart having a set of internal threads engageable and disengagable with the set of external threads at the second end of the pedicle dart fastener to draw the pedicle dart toward the indexed sleeve; the pedicle dart also having a second guide pin through bore sized to freely enable the guide pin to axially pass therethrough, the engagement of the first indexed end of the indexed sleeve and the second indexed end of the pedicle dart for enabling rotational force and displacement of the indexed sleeve to be transmitted to the pedicle dart.

2. The pedicle dart system as recited in claim 1 wherein said an indexed sleeve handle end is "T" shaped.

3. The pedicle dart system as recited in claim 1 wherein said pedicle dart has a self tapping threaded exterior adjacent the first tip end.

4. The pedicle dart system as recited in claim 1 wherein said pedicle dart has plurality of conically tapering exterior ribs adjacent the first tip end.

5. The pedicle dart system as recited in claim 1 wherein said pedicle dart has smooth conically tapering exterior adjacent the first tip end.

6. The pedicle dart system as recited in claim 1 wherein said pedicle dart has a reduced diameter portion near the first tip end to facilitate use as a probe.

7. The pedicle dart system as recited in claim 1 wherein the indexing of the first indexed end of the indexed sleeve is at least a first index sleeve finger and wherein the indexing of the second indexed end of the pedicle dart is at least a first pedicle dart member finger, the interaction between the first index sleeve finger and first pedicle dart member finger transmitting rotational indexing from the indexed sleeve to the pedicle dart.

8. The pedicle dart system as recited in claim 7 wherein the at least a first index sleeve finger is at least a first and a second index sleeve finger, and wherein the at least a first pedicle dart member finger is at least a first and a second pedicle dart member finger and the interaction between the first and second index sleeve fingers and the first and second pedicle dart member fingers transmit rotational indexing from the indexed sleeve to the pedicle dart.

9. A pedicle dart system comprising:
   a guide pin having a first pointed end and a second end opposite the first end;
   a pedicle dart fastener having a manual actuation knob at a first end and a set of external threads at a second end, the pedicle dart fastener having a first guide pin through bore sized to freely enable the guide pin to axially pass therethrough;
   an indexed sleeve having a handle end and a first indexed end, and having a central bore through which the pedicle dart fastener may freely pass limited only by the manual actuation knob of the pedicle dart fastener;
   a pedicle dart having a first tip end and a second indexed end for engaging the first indexed end of the indexed sleeve, the pedicle dart having a set of internal threads engageable and disengagable with the set of external threads at the second end of the pedicle dart fastener to draw the pedicle dart toward the indexed sleeve; the pedicle dart also having a second guide pin through bore sized to freely enable the guide pin to axially pass therethrough, the engagement of the first indexed end of the indexed sleeve and the second indexed end of the pedicle dart for enabling rotational force and displacement of the indexed sleeve to be transmitted to the pedicle dart;

wherein said pedicle dart has plurality of conically tapering exterior ribs adjacent the first tip end.

10. A pedicle dart system comprising:

a guide pin having a first pointed end and a second end opposite the first end;

a pedicle dart fastener having a manual actuation knob at a first end and a set of external threads at a second end, the pedicle dart fastener having a first guide pin through bore sized to freely enable the guide pin to axially pass therethrough;

an indexed sleeve having a handle end and a first indexed end, and having a central bore through which the pedicle dart fastener may freely pass limited only by the manual actuation knob of the pedicle dart fastener;

a pedicle dart having a first tip end and a second indexed end for engaging the first indexed end of the indexed sleeve, the pedicle dart having a set of internal threads engageable and disengagable with the set of external threads at the second end of the pedicle dart fastener to draw the pedicle dart toward the indexed sleeve; the pedicle dart also having a second guide pin through bore sized to freely enable the guide pin to axially pass therethrough, the engagement of the first indexed end of the indexed sleeve and the second indexed end of the pedicle dart for enabling rotational force and displacement of the indexed sleeve to be transmitted to the pedicle dart;

wherein the indexing of the first indexed end of the indexed sleeve is at least a first index sleeve finger and wherein the indexing of the second indexed end of the pedicle dart is at least a first pedicle dart member finger, the interaction between the first index sleeve finger and first pedicle dart member finger transmitting rotational indexing from the indexed sleeve to the pedicle dart.

11. The pedicle dart system as recited in claim 10 wherein the at least a first index sleeve finger is at least a first and a second index sleeve finger, and wherein the at least a first pedicle dart member finger is at least a first and a second pedicle dart member finger and the interaction between the first and second index sleeve fingers and the first and second pedicle dart member fingers transmit rotational indexing from the indexed sleeve to the pedicle dart.

* * * * *